(12) United States Patent
Milliman

(10) Patent No.: US 9,168,042 B2
(45) Date of Patent: Oct. 27, 2015

(54) CIRCULAR STAPLING INSTRUMENTS

(75) Inventor: Keith L. Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 772 days.

(21) Appl. No.: 13/348,958

(22) Filed: Jan. 12, 2012

(65) Prior Publication Data

US 2013/0181035 A1    Jul. 18, 2013

(51) Int. Cl.
*A61B 17/10* (2006.01)
*A61B 17/04* (2006.01)
*A61B 17/115* (2006.01)
*A61B 17/3205* (2006.01)

(52) U.S. Cl.
CPC ....... *A61B 17/1155* (2013.01); *A61B 17/32053* (2013.01)

(58) Field of Classification Search
CPC ................. A61B 2017/07271; A61B 17/1155; A61B 2017/07278; A61B 2017/07285; A61B 2017/07257; A61B 17/0644; A61B 2017/07214; A61B 2017/00473; A61B 2018/1455; A61B 2017/2926; A61B 17/3213
USPC ..................... 227/175.1–182.1; 606/213, 219
See application file for complete search history.

(56) References Cited

U.S. PATENT DOCUMENTS

| | | | | |
|---|---|---|---|---|
| 4,617,928 A * | 10/1986 | Alfranca | ..................... | 227/180.1 |
| 4,881,545 A * | 11/1989 | Isaacs et al. | ................ | 227/178.1 |
| 4,930,674 A * | 6/1990 | Barak | ........................ | 227/179.1 |
| 5,271,543 A | 12/1993 | Grant et al. | | |
| 5,392,979 A * | 2/1995 | Green et al. | ................ | 227/179.1 |
| 5,433,721 A | 7/1995 | Hooven et al. | | |
| 5,632,433 A * | 5/1997 | Grant et al. | ................. | 227/179.1 |
| 6,258,107 B1 * | 7/2001 | Balazs et al. | ................... | 606/153 |
| 6,443,973 B1 | 9/2002 | Whitman | | |
| 6,517,565 B1 | 2/2003 | Whitman | | |
| 6,716,233 B1 | 4/2004 | Whitman | | |
| 6,981,941 B2 | 1/2006 | Whitman et al. | | |
| 7,032,798 B2 | 4/2006 | Whitman et al. | | |
| 7,404,508 B2 | 7/2008 | Smith et al. | | |
| 7,419,080 B2 | 9/2008 | Smith et al. | | |
| 7,959,050 B2 | 6/2011 | Smith et al. | | |
| 8,028,885 B2 | 10/2011 | Smith et al. | | |
| 8,038,046 B2 | 10/2011 | Smith et al. | | |
| 2004/0034367 A1 * | 2/2004 | Malinowski | ......... | A61B 19/201 606/129 |
| 2004/0111081 A1 | 6/2004 | Whitman et al. | | |
| 2005/0187576 A1 | 8/2005 | Whitman et al. | | |
| 2007/0084899 A1 * | 4/2007 | Taylor | ........................ | 227/176.1 |
| 2009/0230170 A1 * | 9/2009 | Milliman | .................... | 227/176.1 |
| 2009/0302093 A1 * | 12/2009 | Kasvikis | .................... | 227/180.1 |
| 2010/0327041 A1 * | 12/2010 | Milliman et al. | .......... | 227/175.1 |
| 2013/0181036 A1 * | 7/2013 | Olson et al. | ................ | 227/180.1 |
| 2013/0200131 A1 * | 8/2013 | Racenet et al. | ............ | 227/180.1 |

FOREIGN PATENT DOCUMENTS

EP    1647231 A1    4/2006
WO   2004112583 A2   12/2004

OTHER PUBLICATIONS

European Search Report EP12198774 dated Apr. 22, 2015.

* cited by examiner

*Primary Examiner* — Robert Long

(57) ABSTRACT

A circular stapling instrument including a stapling forming assembly that is actuated independently from actuation of the cutting assembly is provided. The instrument includes a handle assembly, an elongate body extending from the handle assembly, a cartridge assembly mounted on a distal end of the elongate body. The cartridge assembly includes a pusher assembly and a knife assembly. The knife assembly is selectively fixed relative to the pusher assembly.

18 Claims, 12 Drawing Sheets

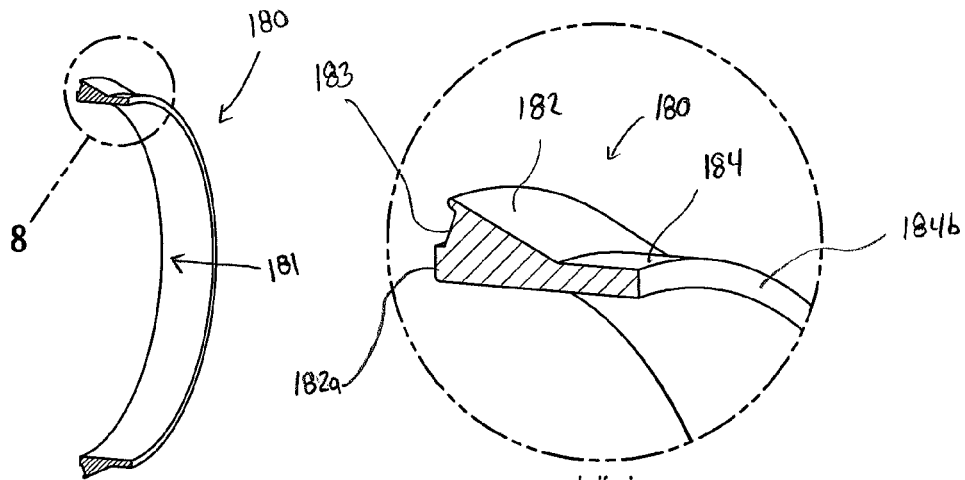
FIG. 7 knife ring
FIG. 8 knife ring
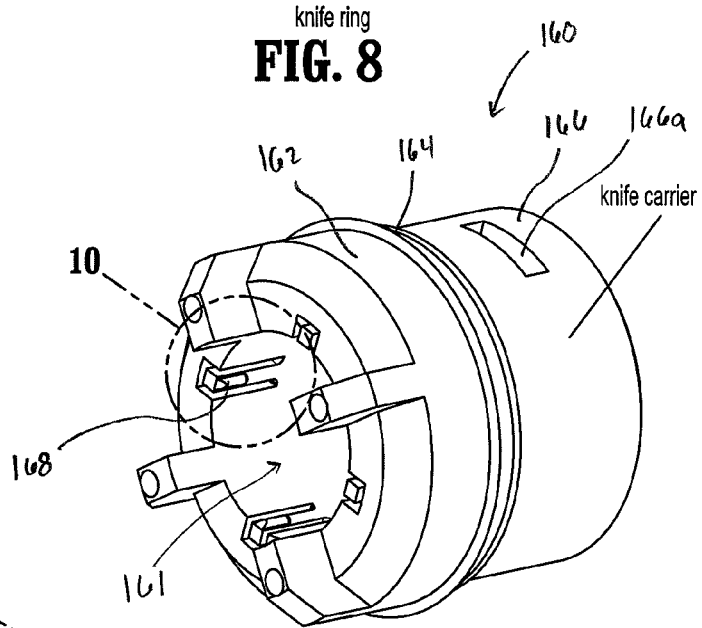
FIG. 9
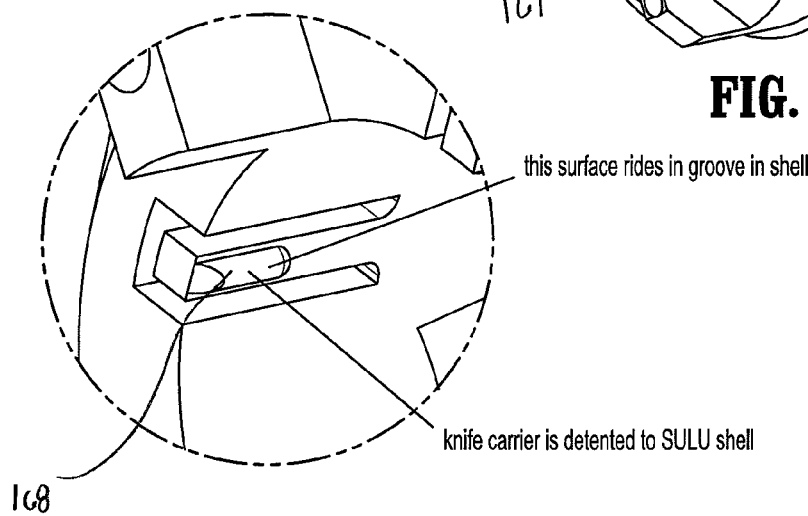
this surface rides in groove in shell
knife carrier is detented to SULU shell
FIG. 10

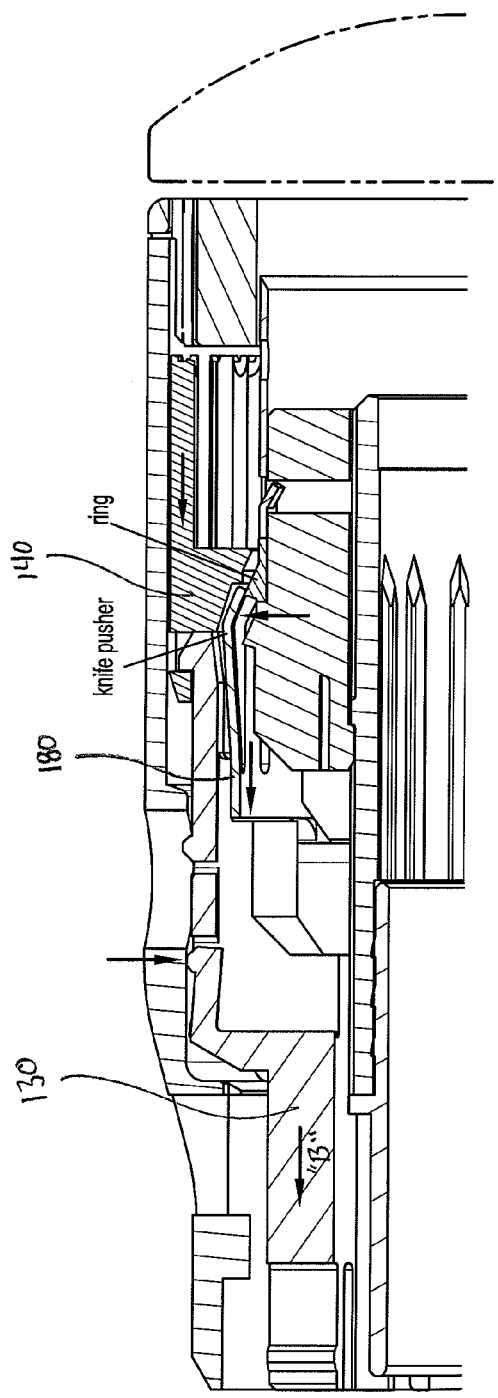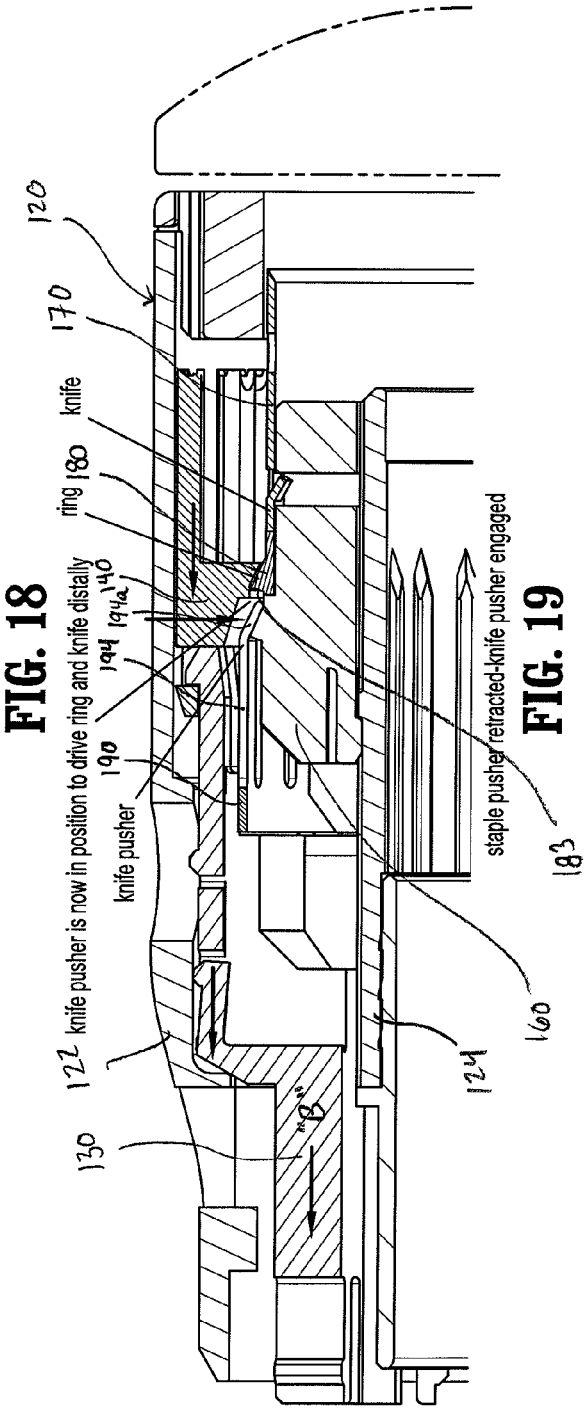

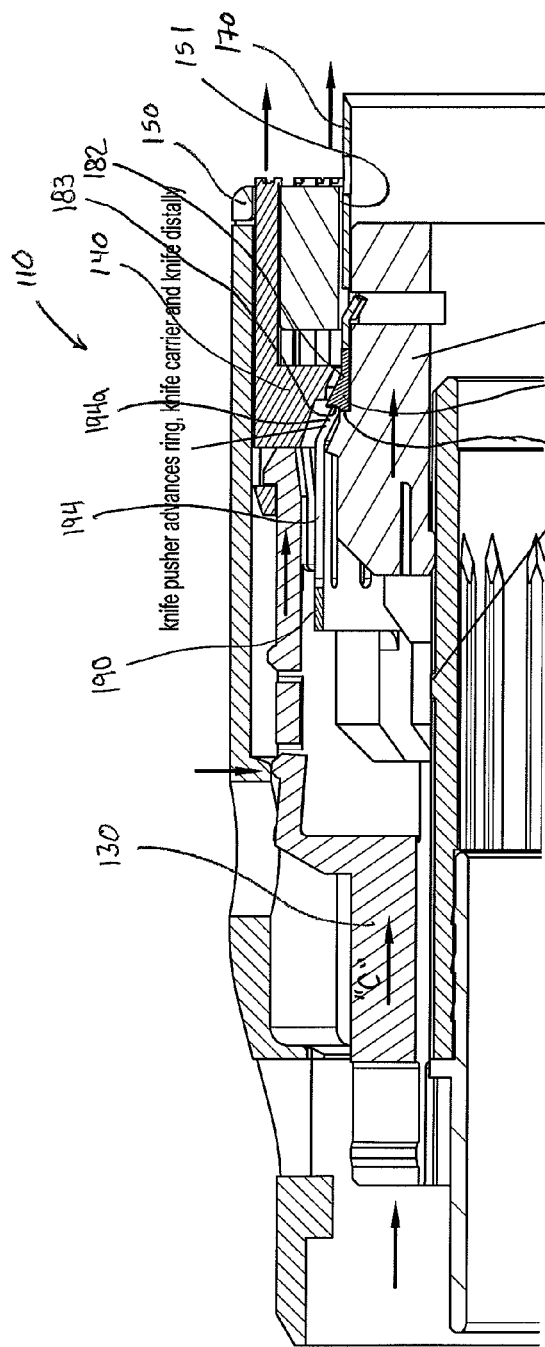
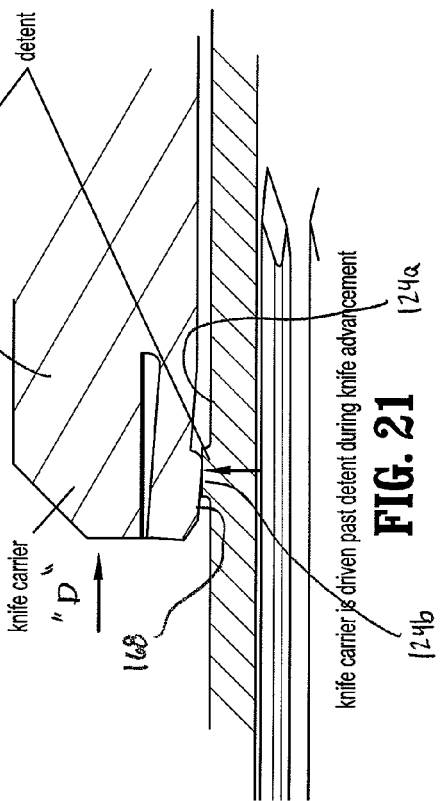
FIG. 20
FIG. 21

CIRCULAR STAPLING INSTRUMENTS

BACKGROUND

1. Technical Field

The present disclosure relates to circular stapling instruments. More particularly, the present disclosure relates to a circular stapling instrument having independent strokes for forming staples and cutting tissue.

2. Background of Related Art

Circular stapling instruments are known, as are their use in closed procedures, endoscopic or laparoscopic procedures or procedures through natural body orifices. Typically the circular staplers include a tool assembly on a distal end of an elongate body. The tool assembly includes a mechanism for forming staples and a knife for cutting the stapled tissue. Actuation of the tool assembly may be performed by a manually operated trigger or a powered drive assembly. Generally, both the actuation of the staple forming mechanism and the advancement of the knife occur at the same time, i.e., simultaneously. Thus, the force provided by the actuation assembly must be sufficient to overcome the force required to form the staples and the force required to advance the knife through the tissue being stapled. Further, the simultaneous actuation of the staple forming mechanism and advancement of the knife requires that the staple forming mechanism and the knife travel the same distance, thereby limiting the staple formation height to the knife travel distance.

Therefore, it would be beneficial to have a circular stapler including a tool assembly configured to form staples independently of cutting tissue.

SUMMARY

Accordingly, a circular stapler including a stapling forming assembly that is actuated independently from actuation of the cutting assembly is provided. In one embodiment, the circular stapler includes a handle assembly, an elongate body extending from the handle assembly, and a cartridge assembly mounted on a distal end of the elongate body. The cartridge assembly includes a pusher assembly and a knife assembly. The knife assembly is selectively fixed relative to the pusher assembly for independent movement relative to the pusher assembly. A knife is initially detached from a knife pusher in a first stroke, and subsequently attached to the knife pusher in a second stroke In one embodiment, the pusher assembly includes a pusher configured to be advanced a first distance and retracted a second distance, the second distance being greater than the first distance. The pusher may include a ridge formed about an inner surface thereof configured to engage a knife pusher. The knife pusher may include a plurality of distally extending fingers. At least one of the plurality of distally extending fingers may include a radially inward extending distal end. The radially inward projecting distal ends of the distally extending fingers may be configured to selectively engage the knife assembly. The knife assembly may include a knife ring having a groove configured to receive the radially inward projecting distal ends of the distally extending fingers during a tissue forming stroke of the circular stapler. The radially inward projecting distal ends of the distally extending fingers may be disposed distal of the groove in the knife ring when the circular stapler is in a first or initial condition.

As will be discussed in further detail below, during the first stroke the pusher assembly may be advanced independently of the knife assembly. The cartridge assembly may include a housing having an outer cylindrical portion and an inner cylindrical portion. The pusher assembly and knife assembly may be selectively received between the inner and outer cylindrical portions of the housing. The inner cylindrical portion may include a plurality of longitudinal grooves on an outer surface thereof configured to operably receive the knife assembly. The inner cylindrical portion may include a detent in each of the plurality of longitudinal grooves configured to selectively engage the knife assembly. In one embodiment, the pusher assembly and the knife assembly are substantially cylindrical.

Also provided is a method of stapling tissue. The method includes the step of providing a surgical stapling instrument having a pusher and a knife assembly, wherein the knife assembly is selectively fixed relative to the pusher for independent movement relative to the pusher. The method also includes the steps of advancing the pusher assembly to cause an ejection and a forming of staples, retracting the pusher assembly and re-advancing the pusher assembly to cause an advancement of the knife assembly and a cutting of tissue. The method may further include the step of providing a lapse of time between the ejection and forming of the staples and the cutting of tissue to allow for tissue normalization. The step of retracting the pusher assembly may include retracting the pusher assembly to a location proximal of an initial location.

DESCRIPTION OF THE DRAWINGS

An embodiment of a circular stapling instrument including a cartridge assembly that is actuated independently from actuation of the cutting assembly is disclosed herein with reference to the drawings, wherein:

FIG. 7 is a cross-sectional perspective view of the knife ring of the knife assembly of FIG. 5;

FIG. 8 is an enlarged sectional view of the indicated area of detail in FIG. 7;

FIG. 9 is a perspective view of the knife carrier of the knife assembly of FIG. 5;

FIG. 10 is an enlarged section view of the indicated area of detail in FIG. 9;

FIG. 18 is cross-sectional side view of a portion of the staple cartridge assembly of FIGS. 11 and 12, as the pusher assembly and knife pusher are retracted;

FIG. 19 is a cross-sectional side view of the portion of the staple cartridge assembly of FIG. 18, upon complete retraction of the pusher assembly and knife pusher;

FIG. 20 is a cross-sectional side view of the portion of the staple cartridge assembly of FIG. 19, upon completion of the firing stroke; and FIG. 21 is an enlarged sectional view of the engagement between the knife carrier and housing of the cartridge assembly of FIG. 20.

DETAILED DESCRIPTION

An embodiment of the presently disclosed circular stapling instrument including independently actuated staple forming and tissue cutting operations will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
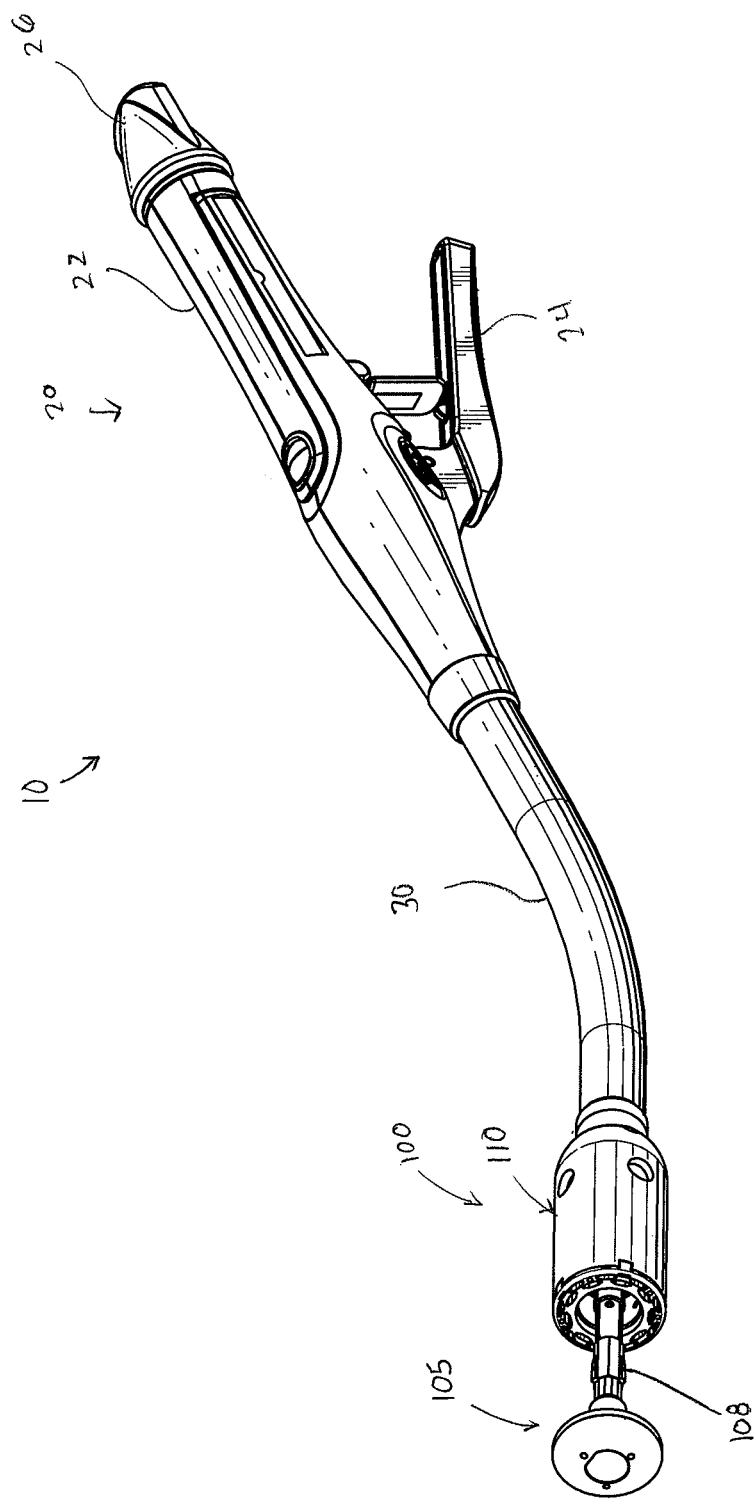
FIG. 1 is a perspective view of a circular stapling instrument including a cartridge assembly according to an embodiment of the present disclosure.

FIG. 1 illustrates an embodiment of a circular stapling instrument according to the present disclosure, shown generally as circular stapler 10. Circular stapler 10 includes a handle assembly 20 and an elongate body 30 extending distally from handle assembly 20. A tool assembly 100 is mounted on a distal end of elongate body 30. Handle assembly 20 includes a fixed handle 22 and a moveable handle or trigger 24. Handle assembly 20 also includes an adjustment knob 26 for moving an anvil assembly 105 relative to cartridge assembly 110. The structure and function of handle assembly 20 will only be described herein to the extent necessary to fully disclose the operation of tool assembly 100. The tool assembly 100 has an anvil assembly 105 including an anvil 106, and a cartridge assembly 110. It is envisioned that tool assembly 100 may be modified for use with any actuation assembly, powered or manual, capable of two independent actuation strokes. It is envisioned that the independent actuation strokes may be completed by the same drive member completing two strokes or by two separate drive members.

Figure 2:
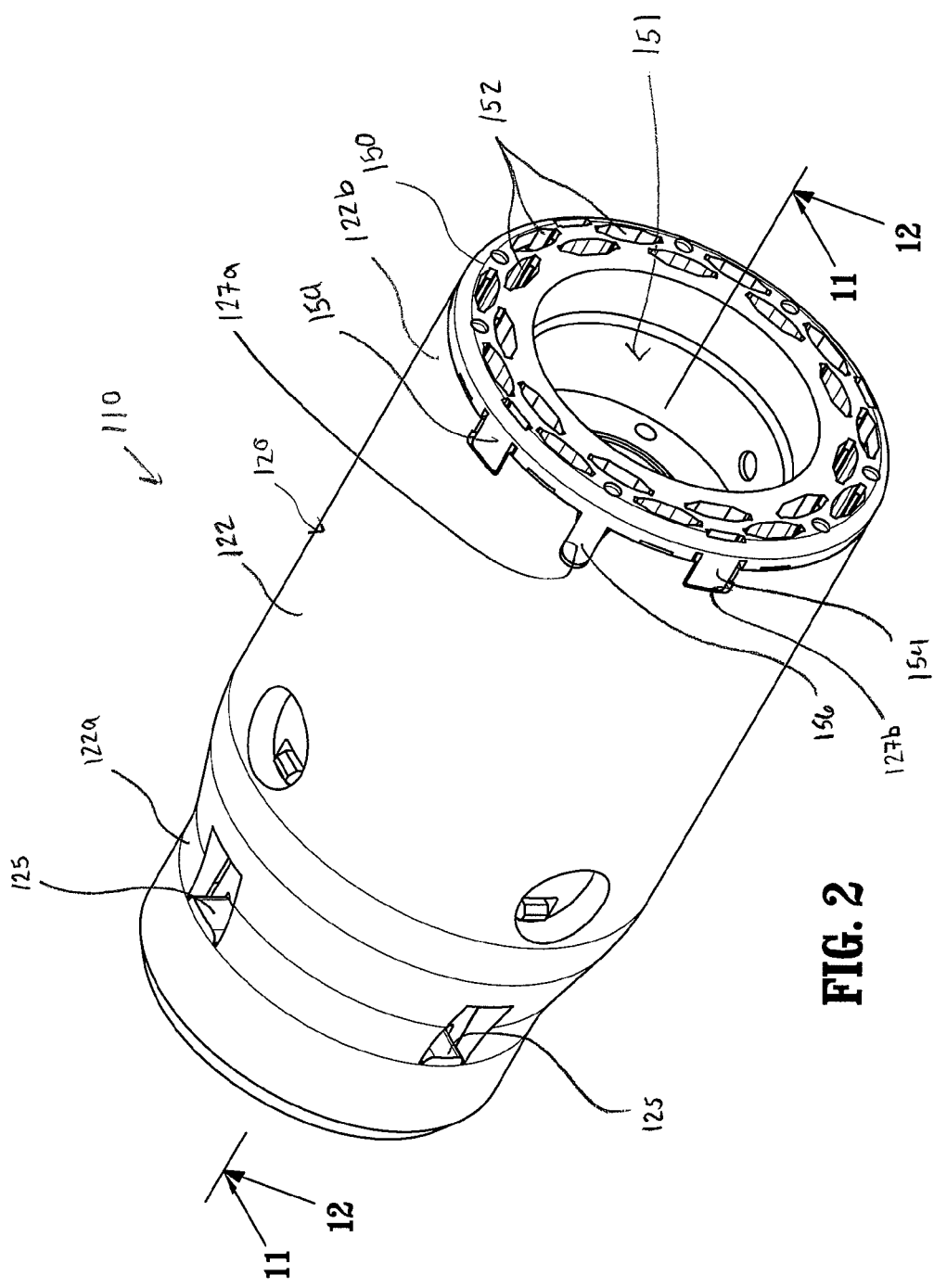
FIG. 2 is an enlarged perspective view of the cartridge assembly of the circular stapling instrument of FIG. 1.

With reference to FIG. 2, cartridge assembly 110 of tool assembly 100 is operably mounted to a distal end of elongate body 30 of circular stapler 10 (FIG. 1). In one embodiment, cartridge assembly 110 is removably secured to elongate body 30 such that cartridge assembly 110, or a portion thereof, may be replaced and circular stapler 10 may be reused. In another embodiment, only a portion of cartridge assembly 110 is configured to be removed, and subsequently replaced or reloaded. Alternatively, circular stapler 10 may be configured for a single use, e.g., disposable. In certain other embodiments, the tool assembly 100 is removable and replaceable.

Figure 3:
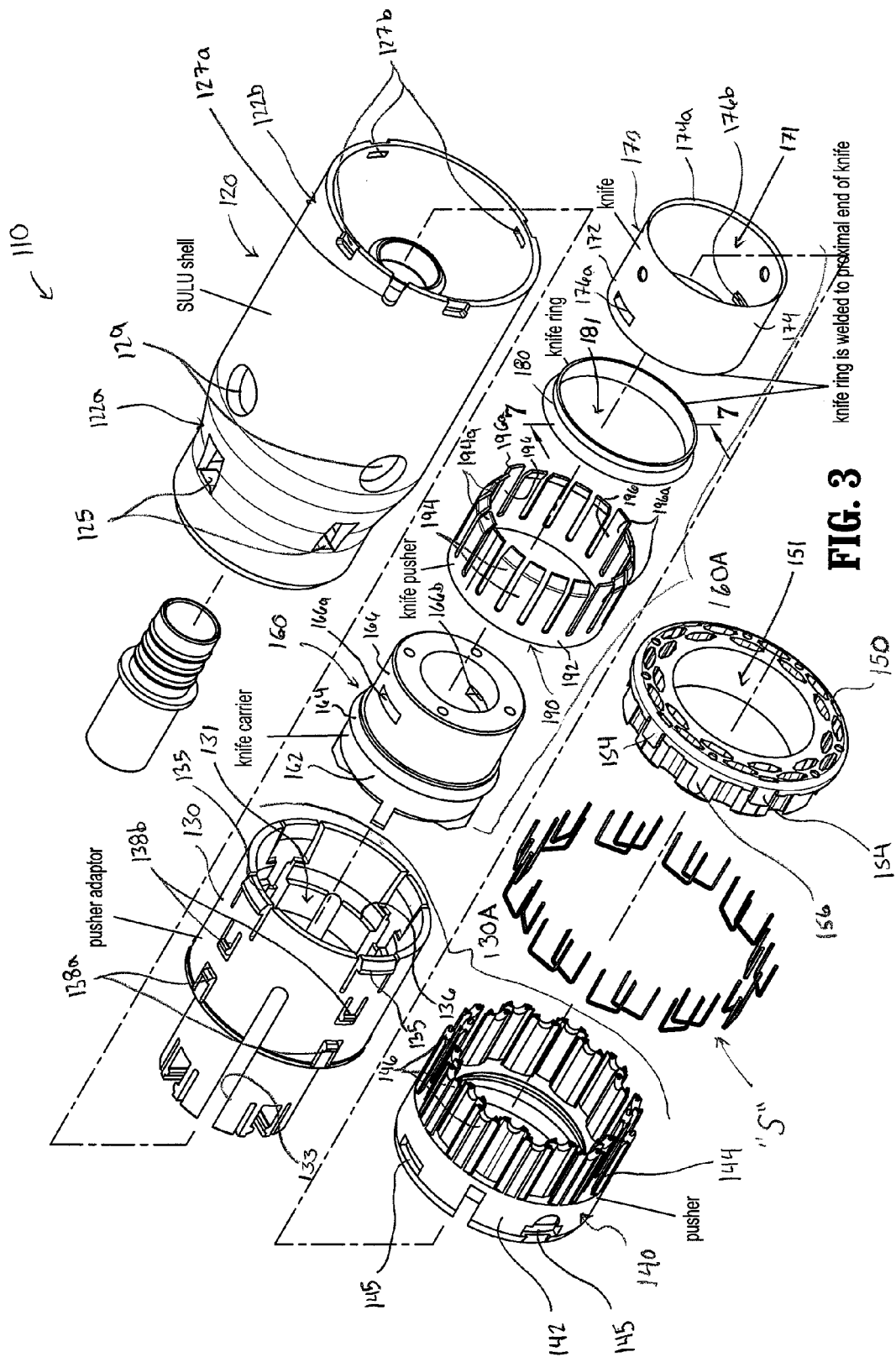
FIG. 3 is an exploded perspective view of the cartridge assembly of FIG. 2.
Figure 16:
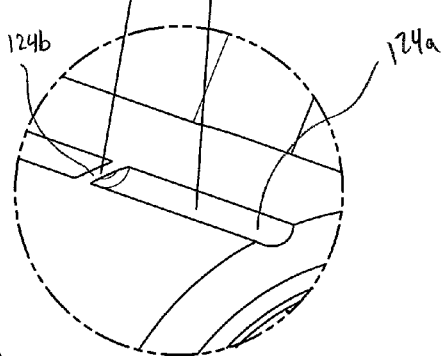
FIG. 16 is an enlarged sectional view of the indicated area of detail in FIG. 15.
Figure 15:
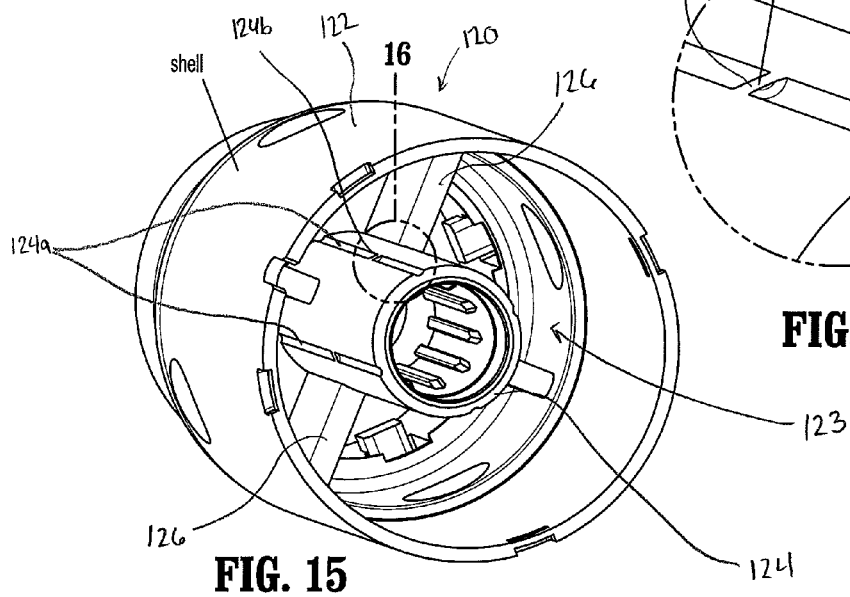
FIG. 15 is a perspective end view of the housing of the cartridge assembly of FIG. 2.

With reference to FIGS. 2 and 3, cartridge assembly 110 includes a housing 120, a pusher assembly 130A, a staple cartridge 150, and a knife assembly 160A. Turning briefly to FIGS. 15 and 16, housing 120 of cartridge assembly 110 includes an outer cylindrical portion 122, an inner cylindrical body 124 and a plurality of radially extending supports or ribs 126 extending between and interconnecting inner cylindrical portion 124 and outer cylindrical portion 122. See FIG. 15. Inner cylindrical portion 124 and outer cylindrical portion 122 are coaxial and define a recess 123 therebetween configured to receive a distal portion of pusher assembly 130A (FIG. 4) and knife assembly 160A (FIG. 5). Inner cylindrical portion 124 of housing 120 includes a plurality of spaced grooves 124a extending longitudinally along an outer surface thereof. Each groove 124a includes a detent 124b. As will be discussed in further detail below, grooves 124a are configured to receive protrusions 168 (FIG. 10) formed on an inner surface of a proximal portion 162 of knife carrier 160. As will also be discussed in further detail below, detents 124b are configured to prevent advancement of knife carrier 160 of knife assembly 160A during a first or staple forming stroke of circular stapler 10.

With reference back to FIG. 3, a proximal end 122a of outer cylindrical portion 122 of housing 120 includes a plurality of tabs 125 formed thereon configured to operably engage cartridge assembly 110 with a distal end of elongate body 30 (FIG. 1). A distal end 122b of outer cylindrical portion 122 of housing 120 defines a plurality of recesses 127b formed thereabout configured to receive mounting tabs 154 of staple cartridge 150. Distal end 122b of outer cylindrical portion 122 of housing 120 also defines a slot 127a configured to receive a projection 156 formed on staple cartridge 150. Slot 127a is positioned such that when projection 156 is received in slot 127a, mounting tabs 154 of staple cartridge 150 are properly aligned with recesses 127b formed in outer cylindrical portion 122 of housing 120. Outer cylindrical portion 122 of housing 120 further defines a plurality of openings 129. As will be discussed in further detail below, each of the plurality of openings 129 is configured to engage a pair of a plurality of detents 138a, 138b formed on a distal portion 134 of pusher adaptor 130.

Figure 4:
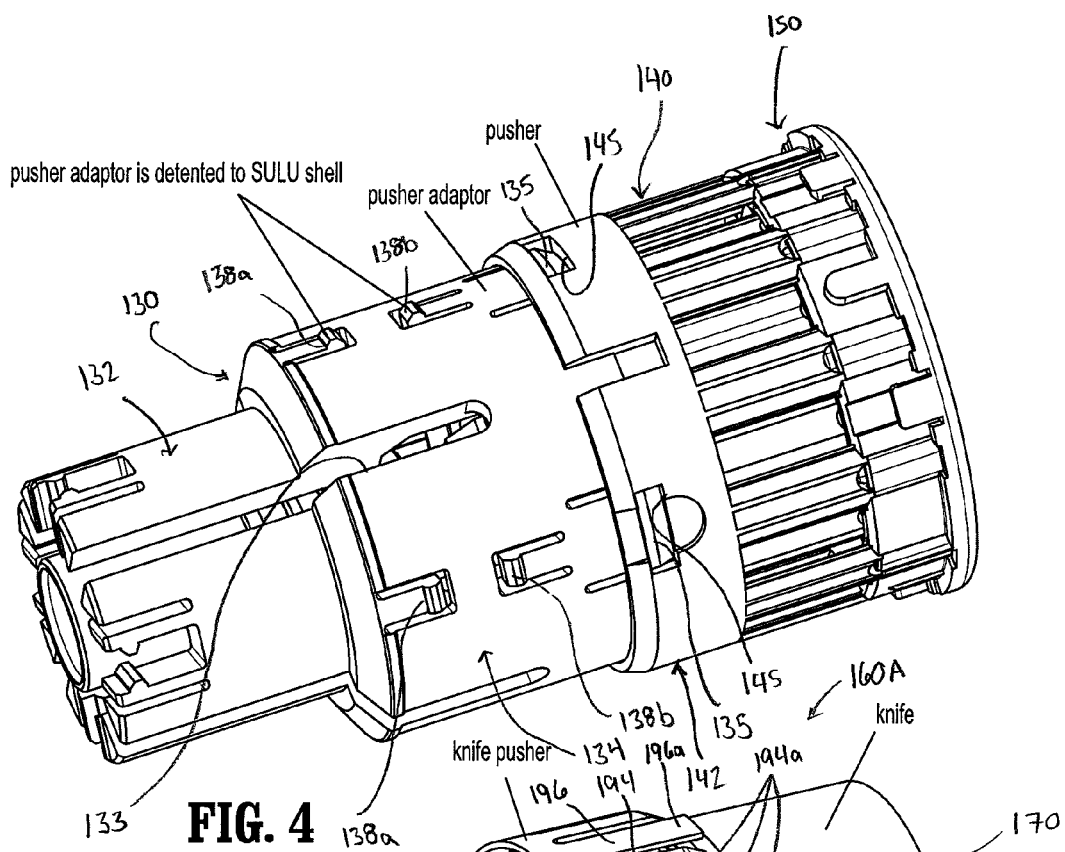
FIG. 4 is perspective view of the pusher assembly and staple cartridge of the cartridge assembly of FIG. 3.
Figure 5:
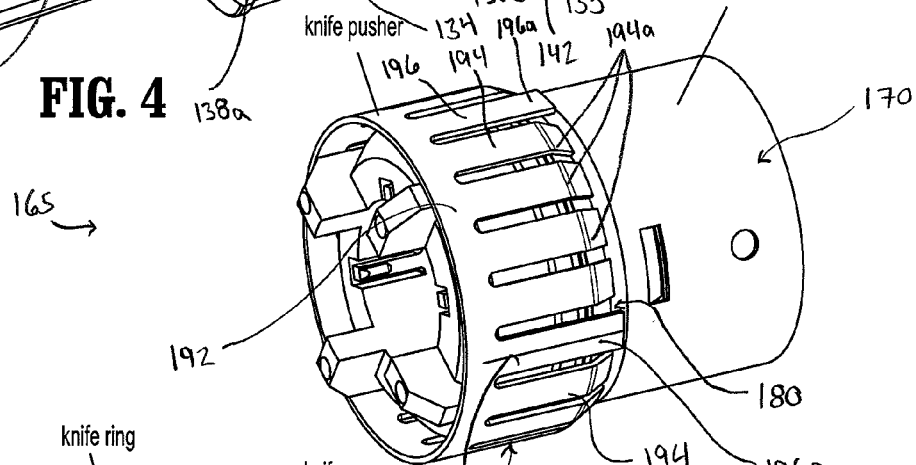
FIG. 5 is a perspective view of the knife assembly of the cartridge assembly of FIG. 3.

With reference now to FIGS. 3 and 4, pusher assembly 130A includes a pusher adaptor 130 and a pusher 140. Pusher adaptor 130 is a substantially cylindrical member having a proximal portion 132 and a distal portion 134. Proximal portion 132 of pusher adaptor 130 is configured for operable engagement with a drive member (not shown). Distal portion 134 of pusher adaptor 130 is configured to operably engage pusher 140. In particular, distal portion 134 includes a plurality of tabs 135 formed therein configured to engage the pusher 140 in recesses 145 formed on a proximal end 142 of pusher 140.

With continued reference to FIGS. 3 and 4, pusher adaptor 130 defines a longitudinal passage 131 extending therethrough. A distal end of longitudinal passage 131 is sized and configured to receive knife assembly 160A in a sliding manner. Pusher adaptor 130 further defines a plurality of longitudinal slots 133 extending along a length thereof. Slots 133 correspond in size and location to supports 126 formed between and interconnecting outer and inner cylindrical portions 122, 124 in housing 120. Pusher adaptor 130 is configured to be received within outer cylindrical portion 122 of housing 120 and about inner cylindrical portion 124 of housing 120. In this manner, slots 133 receive respective supports 126 of housing 120 such that inner cylindrical portion 124 of housing 120 may be received within longitudinal passage 131 of pusher adaptor 130, while allowing the pusher adaptor to move. Pusher adaptor 130 also defines a ledge 136 extending about an inner surface thereof. As will be discussed in further detail below, ledge 136 is configured to engage a proximal end 192 of knife pusher 190 during advancement of pusher assembly 130A. As discussed above, pusher adaptor 130 includes a plurality of paired detents 138a, 138b configured to be selectively received within openings 129 formed in outer cylindrical portion 122 of housing 120.

With reference back to FIG. 3, pusher 140 includes a proximal portion 142 and a distal portion 144. Proximal portion 142 of pusher 140 defines a plurality of recesses 145 configured to selectively engage tabs 135 formed on distal portion 134 of pusher adaptor 130. As will be discussed in further detail below, pusher 140 does not engage pusher adaptor 130 until the first stroke, or staple forming stroke, of circular stapler 10. The distal advancement of pusher adaptor 130 during the first stroke causes engagement of tabs 135 formed on distal portion 134 of pusher adaptor 130 within recesses 145 formed in proximal portion 142 of pusher 140. Engagement of pusher adaptor 130 with pusher 140 allows pusher 140 to be retracted along with pusher adaptor 130 at the completion of the firing stroke. Pusher assembly 130A is configured such that retraction of pusher adaptor 130 subsequent to the staple forming stroke retracts pusher 140 to a position proximal of its initial position.

As will also be discussed in further detail below, at the completion of the second stroke, or cutting stroke, of circular stapling device 10 pusher assembly 130A is completely retracted relative to housing 120. In the completely retracted position, pusher 140 is disengaged from pusher adapter 130. In this manner, pusher 140 and staple cartridge 150 may be separated from housing 120. Proximal portion 142 of pusher 140 is further configured to engage a distal end 194a, 196a of fingers 194, 196, respectively to retract knife pusher 190 as pusher 140 is retracted subsequent to the staple forming stroke and the tissue cutting stroke. Distal portion 144 of pusher 140 includes a plurality of pusher members 146 extending distally therefrom and arranged in at least one concentric row: the pusher members in FIG. 3, for example, have two concentric rows. Pusher members 146 align with staples "S" received within staple cartridge 150 such that advancement of pusher 140 relative to staple cartridge 150 causes ejection of staples "S" from staple cartridge 150.

With reference to FIGS. 2 and 3, staple cartridge 150 is a substantially cylindrical member configured to operably engage distal end 122b of outer cylindrical portion 122 of housing 120 and defines a longitudinal opening 151 configured to receive a distal portion of knife assembly 160A therethrough. Staple cartridge 150 includes a plurality of staple receiving pockets 152 disposed about opening 151 arranged in at least one concentric row: for example, in FIG. 3, the pockets have two concentric rows. Staple receiving pockets 152 align with pusher members 146 formed on distal portion 144 of pusher 140. As discussed above, staple cartridge 150 also includes a plurality of mounting tabs 154 and protrusion 156. Mounting tabs 154 operably engage staple cartridge 150 with distal portion 122b formed in outer cylindrical portion 122 of housing 120 and protrusion 156 assures the proper alignment of staple cartridge 150 with outer cylindrical portion 122 of housing 120.

Figure 6:
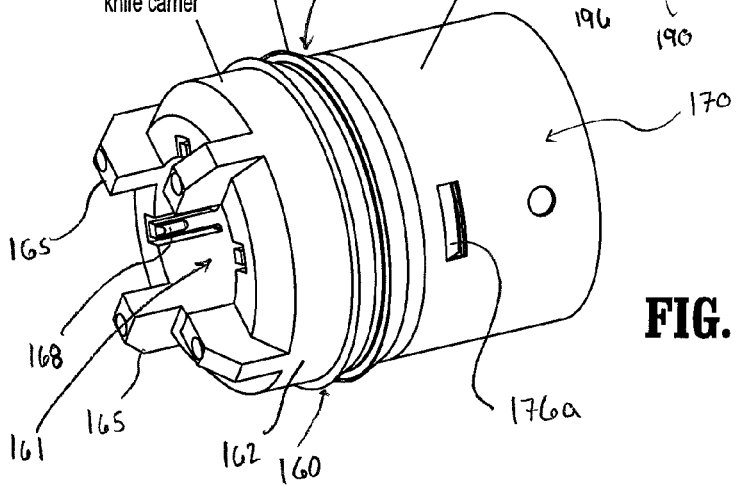
FIG. 6 is a perspective view of the knife carrier, circular knife and knife ring of the knife assembly of FIG. 5.

With reference now to FIGS. 3, 5 and 6, knife assembly 160A includes a knife carrier 160, a circular knife 170, a knife ring 180 and a knife pusher 190. With particular reference to FIG. 9, knife carrier 160 is a substantially cylindrical member having a proximal portion 162, a distal portion 166 and an annular ridge 164 formed therebetween. Knife carrier 160 defines a longitudinal passage 161 extending therethrough. As will become apparent, longitudinal passage 161 is sized and configured to receive a mounting portion 108 of anvil assembly 105 (FIG. 1) therethrough. Proximal portion 162 of knife carrier 160 includes a plurality of spacers 165 configured to engage supports 126 extending between and interconnecting inner and outer cylindrical portions 122, 124 of housing 120. Proximal portion 162 of knife carrier 160 further includes a plurality of protrusions 168 extending radially inwardly from an inner surface thereof. As will be discussed in further detail below, protrusions 168 are configured to be received within grooves 124a (FIGS. 15 and 16) extending longitudinally along the outer surface of inner cylindrical portions 124 of housing 120. Accordingly, protrusions 168 correspond in number and position to grooves 124a. Protrusions 168 are configured to engage detents 124b formed within each of grooves 124a to prevent knife assembly 160A from advancing distally during the first or staple forming operation of circular stapler 10.

Figure 11:
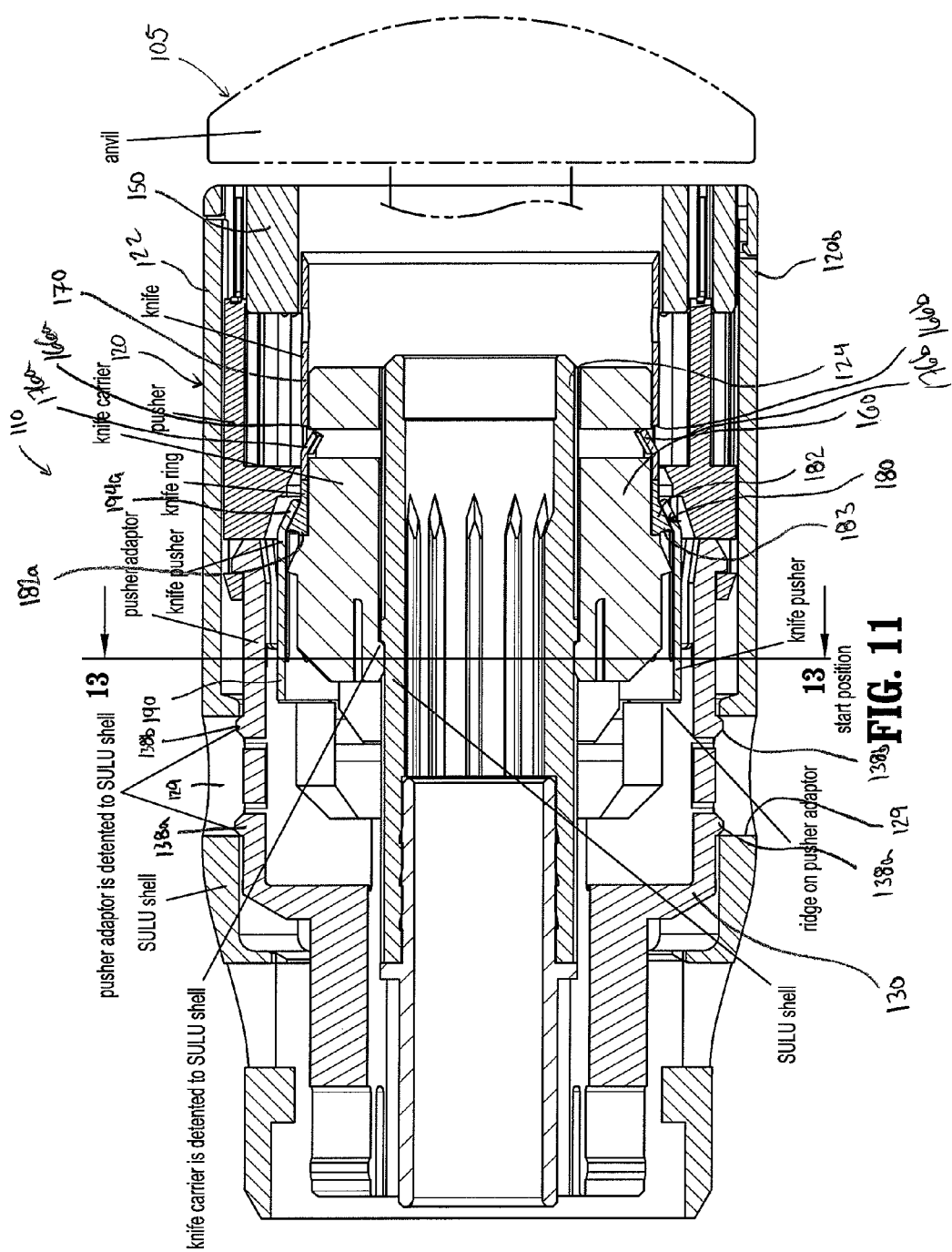
FIG. 11. is a cross-sectional view of the cartridge assembly of FIG. 2, in an initial position, taken along line 11-11 of FIG. 2.

With continued reference to FIG. 9, annular ridge 164 extends radially outward from between proximal and distal portions 162, 166 of knife carrier 160. Annular ridge 164 is configured to engage a proximal end of knife ring 180. Distal portion 166 of knife carrier 160 is configured to receive knife ring 180 and circular knife 170 thereabout. In particular, as seen in FIGS. 3 and 11, distal portion 166 defines a pair of opposed recesses 166a, 166b configured to engage respective locking tabs 176a, 176b formed on knife 170.

With particular reference still to FIG. 3, knife 170 is a substantially cylindrical member having proximal and distal ends 172, 174 and defining a longitudinal opening 171 extending therethrough. Knife 170 is sized and configured to be received through longitudinal opening 141 of staple cartridge 140. Distal end 174 of knife 170 includes a sharpened surface 174a defining a knife edge configured for cutting tissue. As discussed above, proximal end 172 of knife 170 is configured to be received about distal portion 166 of knife carrier 160 and includes a pair of opposed tabs 176a, 176b configured to be received within respective recesses 166a, 166b formed in distal portion 166 of knife carrier 160.

With reference to FIGS. 6-8, knife ring 180 is a substantially cylindrical member having proximal and distal portions 182, 184 and defining a longitudinal passage 181 therethrough. Proximal portion 182 flares radially outward and defines a groove 183 extending about a proximal end or surface 182a of thereof. See FIG. 8. An inner portion of proximal end 182a is configured to engage annular ridge 164 of knife carrier 160 when knife ring 180 is received about distal portion 166 of knife carrier 160. Proximal portion 182 is configured such that groove 183 is disposed radially outward of annular ridge 164. The knife ring has at least one finger, and may have a plurality of fingers 194. As will be discussed in detail below, groove 183 is configured to receive inwardly extending distal ends 194a of distally extending finger or fingers 194. A distal end 184b of distal portion 184 of knife ring 180 is configured to engage proximal end 172 of knife 170. Knife ring 180 may be secured to knife 170 using adhesives, welding or other any other suitable method.

With reference now to FIGS. 3 and 5, knife pusher 190 is a substantially cylindrical body having a base 192 and a plurality of distally extending fingers 194, 196. Distally extending fingers 194 include inwardly extending distal ends 194a and distally extending fingers 196 include substantially straight distal ends 196a. Both inwardly projecting distal ends 194a of distally extending fingers 194 and substantially straight distal ends 196a of distally extending fingers 196 are configured to engage pusher 140 during retraction of pusher assembly 130A subsequent to the staple forming stroke. Only distal ends 196a of distally extending fingers 196 are configured to engage pusher 140 during retraction of pusher assembly 130A subsequent to the tissue cutting stroke. Knife pusher 190 is configured to be received over proximal portion 172 of knife carrier 170. As discussed above, inwardly extending distal ends 194a of distally extending fingers 194 are configured to engage groove 183 formed in proximal end 182a of proximal portion 182 of knife ring 180 (FIG. 8). In a first or initial condition, knife pusher 190 is received about proximal portion 162 of knife carrier 160 such that distal ends 194a of distally extending fingers 194 are received about an outer surface of flared proximal portion 182 of knife ring 180. As will be discussed in further detail below, in this configuration, fingers 194 of knife pusher 190 are able to slide over knife ring 180 and circular knife 170 during advancement of pusher assembly 130A.

Figure 12:
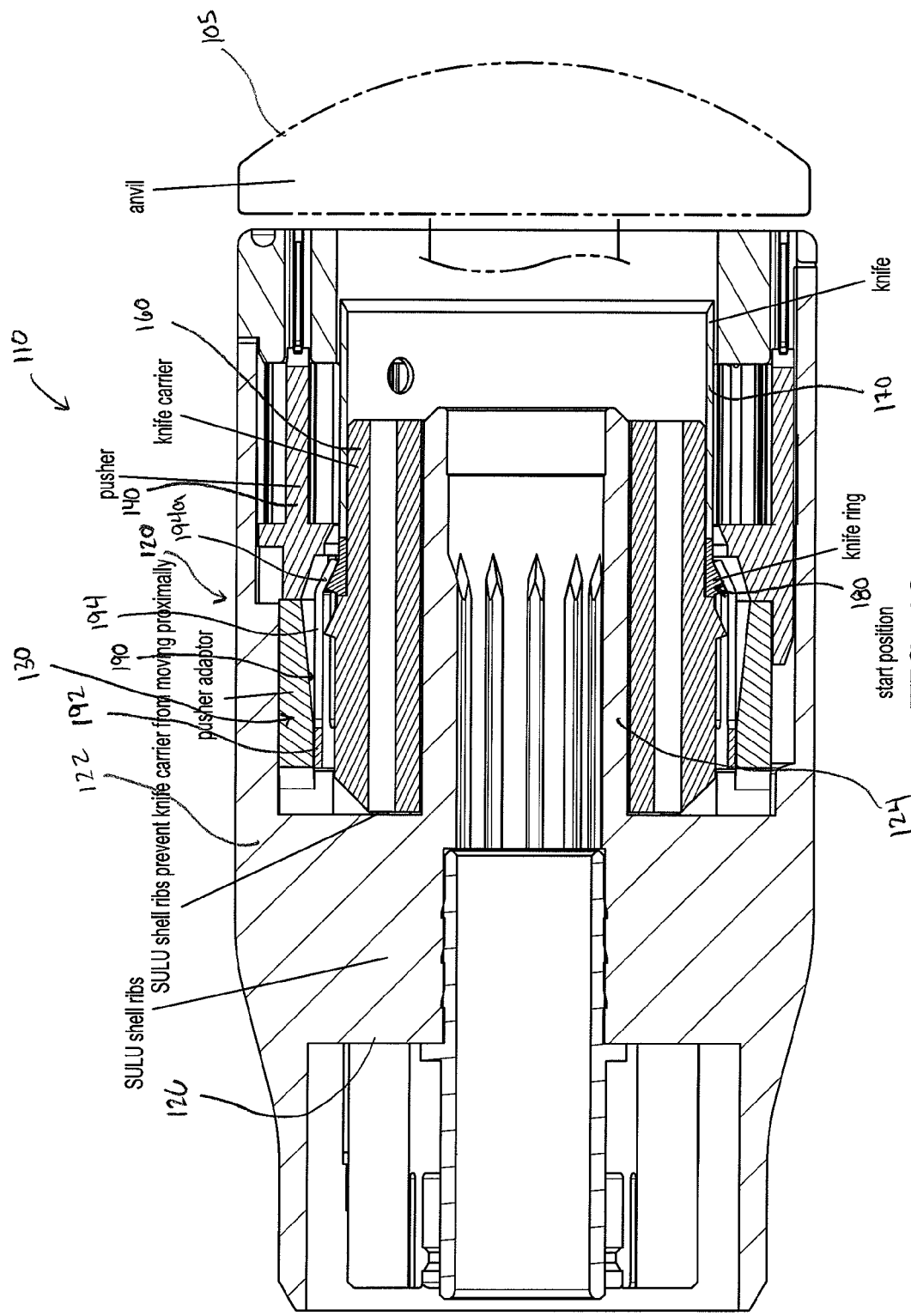
FIG. 12 is a cross-sectional view of the cartridge assembly of FIG. 2, in the initial position, taken along line 12-12 of FIG. 2.
Figure 13:
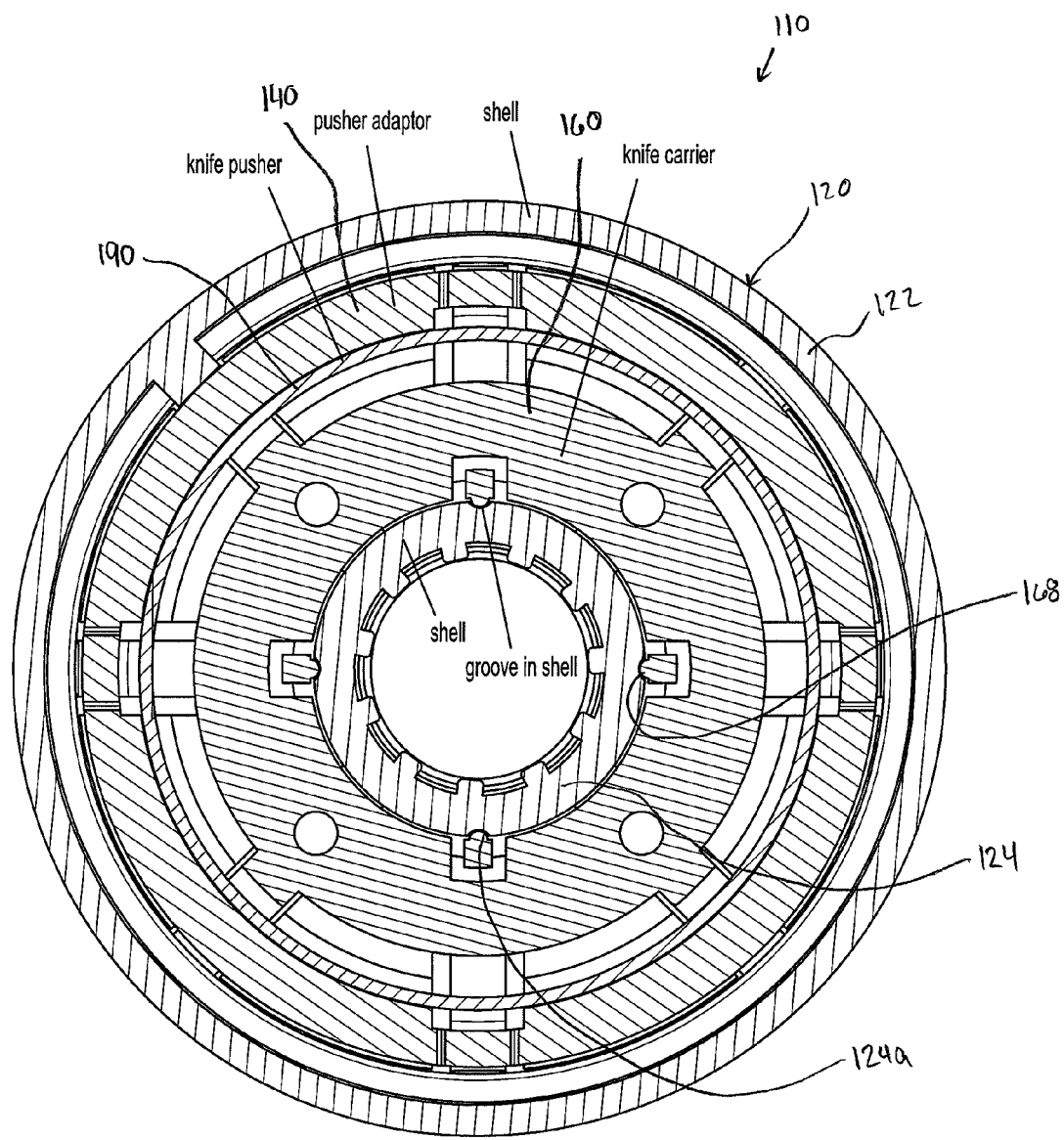
FIG. 13 is a cross-sectional view of the cartridge assembly of FIGS. 11 and 12, in the initial position, taken along line 13-13 of FIG. 11.
Figure 14:
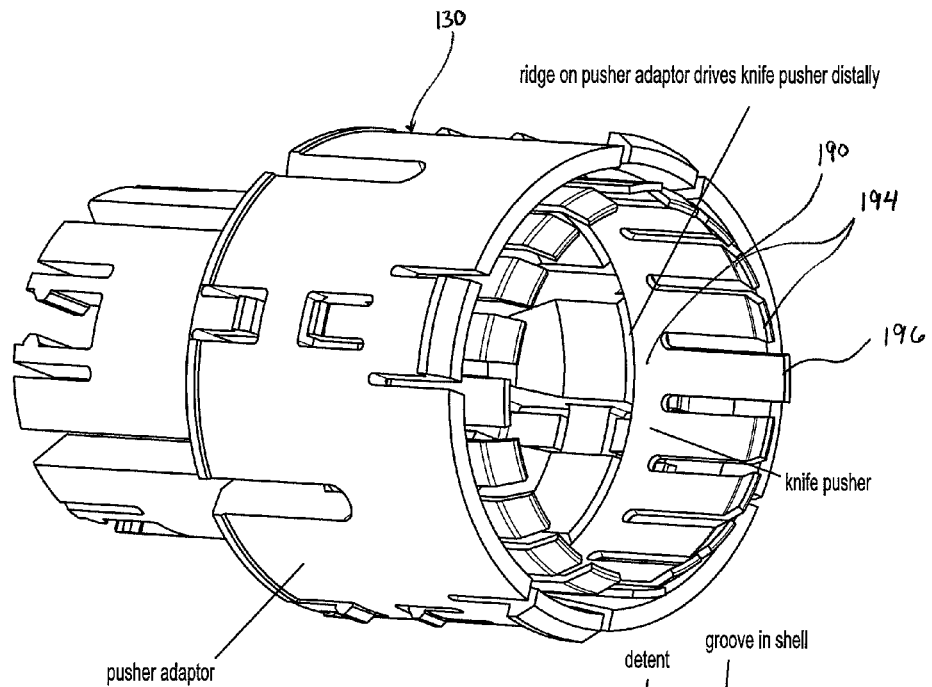
FIG. 14 is a perspective view of the pusher adaptor of the pusher assembly of FIG. 4 and the knife pusher of the knife assembly of FIG. 5.

The operation of cartridge assembly 110 will now be described with reference to FIGS. 11-21. Referring initially to FIGS. 11-13, cartridge assembly 110 is shown in a first or initial condition. In the initial condition, pusher assembly 130A is received between outer and inner cylindrical portions 122, 124 of housing 120. Knife assembly 160A is received within longitudinal passage 131 of pusher adaptor 130 and about inner cylindrical portion 124 of housing 120. Staple cartridge 150 is in operative engagement with distal end 120b of housing 120 to operably retain pusher assembly 130A and knife assembly 160A within housing 120. Knife pusher 190 is positioned such that distal ends 194a of distally extending fingers 194 are received about flared proximal portion of 182 knife ring 180 and are disposed distal of groove 183 formed in distal end 182a thereof. The distal position of distal ends 194a of fingers 194 relative to groove 183 permits distal advancement of knife pusher 190 relative to knife carrier 160, circular knife 170 and knife ring 180. In this manner, pusher assembly 160A and knife pusher 190 may be advanced distally without causing the advancement of circular knife 170.

In the first or initial position, pusher assembly 130A is prevented from inadvertent distal advancement relative to housing 120 through engagement of the plurality of paired detents 138a, 138b formed on distal portion 134 of pusher adaptor 130 with openings 129 formed in outer cylindrical portion 122 of housing 120.

Figure 17:
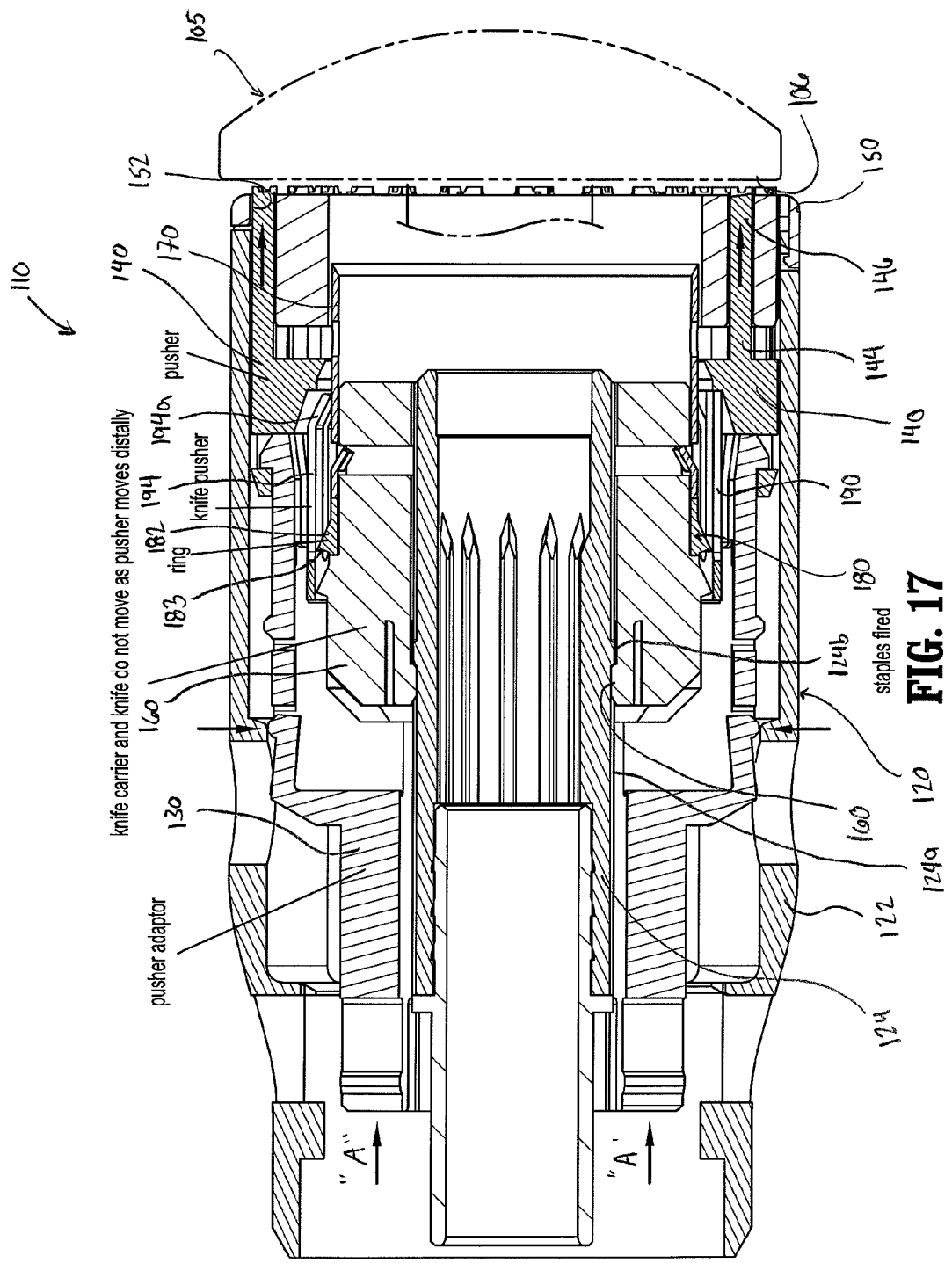
FIG. 17 is a cross-sectional side view of the cartridge assembly of FIGS. 11 and 12, upon completion of the staple forming stroke.

With reference now to FIG. 17, during a first or staple forming stroke of circular stapler 10 (FIG. 1), following approximation of anvil assembly 105 against cartridge assembly 110, retraction or actuation of trigger 24 relative to handle 22 causes advancement of a drive assembly (not shown) which operably engages pusher adaptor 130 to cause the advancement of pusher assembly 130A, as indicated by arrows "A". Advancement of pusher adaptor 130 advances pusher 140 thereby causing pusher members 146 on distal portion 144 thereof to be advanced into staple receiving pockets 152 of staple cartridge 150 and to eject staples "S" from staple cartridge 150. Although not shown, the ejection of staples "S" from staple cartridge 150 causes advancement of staples "S" into an anvil 106 of anvil assembly 105 that has recesses shaped to form the staples "S", thereby securing the tissue retained between the staple cartridge 150 and anvil assembly 105.

During the stapling stroke, advancement of pusher assembly 130A also causes distal advancement of knife pusher 190. Since distal ends 194a of distally extending fingers 194 of knife pusher 190 are disposed outward of flared proximal portion 182 of knife ring 180 and distally of groove 183 formed therein, knife pusher 190 is free to move distally relative to knife carrier 160, circular knife 170 and knife ring 180. Knife carrier 160 is maintained relative to housing 120 through engagement of protrusions 168 of knife carrier 160 with detents 124b formed in grooves 124a of inner cylindrical portion 124 of housing 120.

With reference to FIGS. 18 and 19, upon completion of the firing stroke, pusher assembly 130A and knife pusher 190 are retracted proximally relative to housing 120, as indicated by arrows "B", to a position proximal of its initial position prior to the staple forming stroke. Knife pusher 190 is sufficiently retracted relative to knife carrier 160 and knife ring 180 such that distal ends 194a of distally extending fingers 194 of knife pusher 190 slide over the proximal portion 182, which is flared outwardly, of ring 180, expanding the fingers in the radial direction. Then, the fingers resiliently move into position behind the proximal portion 182 so that they are disposed proximally of knife ring 180. For example, the fingers move into position behind the groove 183. (FIG. 19)

With reference now to FIGS. 20 and 21, during the second or cutting stroke of circular stapler 10, a second retraction or actuation of trigger 24 relative to handle 26 causes advancement of the drive member (not shown) which operably engages pusher adaptor 130 to cause the advancement of pusher assembly 130A, as indicated by arrows "C". Advancement of pusher adaptor 130 causes advancement of knife pusher 190. Advancement of knife pusher 190 causes engagement of distal ends 194a of distally extending fingers 194 to engage groove 183 formed in proximal end 182a of proximal portion 182 of knife ring 180. In this manner, advancement of knife pusher 190 also causes the advancement of knife carrier 160, circular knife 170 and knife ring 180, as indicated by arrows "D". Advancement of knife assembly 160A relative to staple cartridge 150 causes knife 170 to be received through longitudinal opening 151 of staple cartridge 150, thereby severing the tissue retained between staple cartridge 150 and anvil 105. Retraction of the drive assembly (not shown) causes the retraction of pusher assembly 130A and knife assembly 160A.

The use of circular stapler 10 will now be described with reference to the figures, namely FIGS. 17-21. In use, circular stapler 10 is operated in a manner substantially similar to a traditional circular stapler. Once oriented such that the tissue to be stapled is received between cartridge assembly 110 and anvil assembly 105 and anvil assembly 105 is approximated towards cartridge assembly 110, trigger 24 may be squeezed to cause the actuation of handle assembly 20. As discussed above, actuation of handle assembly 20 causes a first advancement of a drive assembly (not shown) which causes the advancement of pusher assembly 130A. During the first or staple forming stroke, pusher assembly 130A and knife pusher 190 are moved relative to housing 120 and knife carrier 160, circular knife 170 and knife ring 180 such that only the staple forming function is performed. Accordingly, the force required for completion of the first stroke of circular stapler 10 does not include the force necessary to also cut the tissue simultaneously therewith.

Upon completion of the first or staple forming stroke, trigger 24 is released to permit the retraction of the drive member and pusher assembly 130A. As discussed above, pusher assembly 130A and knife pusher 190 are retracted to a position proximal of their initial positions. In one embodiment, pusher assembly 130A is retracted 0.065 inches further back from its initial starting position. In this retracted position, distal ends 194a of distally extending fingers 194 of knife pusher 190 are disposed proximal of proximal end 182a of proximal portion 182 of knife ring 180.

A subsequent squeezing or actuation of trigger 24 causes a second advancement of the drive member and pusher assembly 130A. Advancement of pusher assembly 130A and knife pusher 190 causes distal ends 194a of distally extending fingers 194 of knife pusher 190 to be received within groove 183 formed in proximal end 182a of proximal portion 182 of knife ring 180. Accordingly, advancement of knife pusher 190 causes the advancement of knife carrier 160, circular knife 170 and knife ring 180. Advancement of circular knife 170 causes the cutting of tissue positioned between cartridge assembly 110 and anvil assembly 105. Because staples "S" were ejected and formed during the first stroke of circular stapler 10, the force required to complete the second or cutting stroke of circular stapler 10 is less then the force necessary to complete both the staple ejecting/forming and tissue cutting procedure. The protrusions 168 on the knife carrier are movable and the force provided by the drive member during the second stroke is sufficient to disengage protrusions 168 formed on knife carrier 160 from detents 124b formed on the outer surface of inner cylindrical portion 122 of housing 120 such that knife assembly 160A, in its entirety, is permitted to advance distally relative to housing 120.

Upon completion of the tissue cutting stroke, pusher assembly 130A and knife assembly 160A are retracted proximally to the initial position. Retraction of pusher assembly 130A to an initial position causes disengagement of pusher 140 from pusher adaptor 130, via the engagement of the detent 138b with the outer cylindrical portion 122. In this manner, pusher 140 and empty staple cartridge 150 may be separated from housing 120 and replaced.

In addition to the reduced force requirements provided by the two stroke operation of circular stapler 10, the independent or decoupled staple forming and tissue cutting function of circular stapler 10 also permits the varying of the staple crimp height relative to the knife travel distance, the varying of the staple travel speed relative to the knife travel speed, and the addition of a dwell time between staple formation and tissue cutting. This configuration allows a clinician to optimize staple crimp heights to given conditions, such as, tissue thickness, tissue compliance and clamping force. The handle of the circular stapling instrument can include an indicator that shows the user of the instrument the relative crimp size of the staples. A knob may be provided on the handle or housing to adjust the stroke of the pusher and thereby effect a different crimped staple size. This configuration may also allow for the monitoring of staple forming and knife cutting forces, to alert the clinician in case an abnormal force is detected. This configuration further allows force and other data to be monitored and used for data collection and research, which when analyzed, may lead to further optimization of operational parameters, such as staple crimp height and dwell and travel speed. The instrument may have a controller that stores such data and/or provides indications concerning such data. The controller can be included in the instrument housing, or the instrument can be connected to the controller by wires or wireless connection. By independently controlling and optimizing these various parameters, improved hemostasis and anastomonic joint strength may result across a much broader range of tissue thicknesses, thereby allowing a clinician to have improved and customized control over the results. Further still, when the stapling and cutting functions are performed at the same time, the tissue being stapled may be displaced by the knife, thereby causing the staple legs to deflect and misalign with their intended anvil pockets and resulting in poor staple formation and possible leakage.

It will be understood that various modifications may be made to the embodiment disclosed herein. For example, circular stapler 10 may include a mechanism for changing cartridge assembly 110 from two stroke operation to a single stroke operation. Therefore, the above description should not be construed as limiting, but merely as exemplifications of particular embodiments. Those skilled in the art will envision other modifications within the scope and spirit of the claims appended hereto.

The invention claimed is:

1. A circular stapler comprising:
a handle assembly;
an elongate body extending from the handle assembly; and,
a cartridge assembly mounted on a distal end of the elongate body, the cartridge assembly including a pusher assembly and a knife assembly, the knife assembly including a knife pusher and a knife, wherein the knife is selectively fixed relative to the knife pusher and the pusher assembly and mounted for independent movement of the knife pusher and the pusher assembly relative to the knife, the knife being detached from the knife pusher and the pusher assembly in a first stroke, and attached to the knife pusher and the pusher assembly in a second stroke, wherein the knife pusher is advanced a first distance during the first stroke and retracted a second distance following the first stroke, the second distance being greater than the first distance.

2. The circular stapler of claim 1, wherein the pusher assembly includes a pusher having a ridge formed about an inner surface thereof configured to engage the knife pusher.

3. The circular stapler of claim 1, wherein the knife pusher includes a distally extending finger.

4. The circular stapler of claim 3, wherein the distally extending finger includes a radially inward extending distal end.

5. The circular stapler of claim 4, wherein the radially inward projecting distal end of the distally extending finger is configured to selectively engage the knife.

6. The circular stapler of claim 5, further comprising a knife ring having a groove configured to receive the radially inward projecting distal end of the distally extending finger during a tissue forming stroke of the circular stapler.

7. The circular stapler of claim 6, wherein the radially inward projecting distal end of the distally extending finger is disposed distal of the groove in the knife ring when the circular stapler is in a first or initial condition.

8. The circular stapler of claim 3, wherein the knife is attached to a knife ring having an outwardly flared proximal portion.

9. The circular stapler of claim 8, wherein the finger of the knife pusher slides over the proximal portion of the knife ring, expanding the finger in the radial direction.

10. The circular stapler of claim 9, wherein the proximal portion of the knife ring defines a groove for receiving the finger.

11. The circular stapler of claim 1, wherein during the first stroke the pusher assembly is advanced independently of the knife.

12. The circular stapler of claim 1, wherein the cartridge assembly includes a housing having an outer cylindrical portion and an inner cylindrical portion.

13. The circular stapler of claim 12, wherein the pusher assembly and the knife are selectively received between the inner and outer cylindrical portions of the housing.

14. The circular stapler of claim 13, wherein the inner cylindrical portion includes a detent configured to engage the knife assembly and prevent movement of the knife.

15. The circular stapler of claim 14, wherein the knife is attached to a knife carrier having a movable protrusion to allow the knife carrier to move past the detent.

16. The circular stapler of claim 1, wherein the pusher assembly and the knife are substantially cylindrical.

17. A circular stapler comprising:
a handle assembly;
an elongate body extending from the handle assembly; and, a cartridge assembly mounted on a distal end of the elongate body, the cartridge assembly including a pusher assembly and a knife assembly, the knife assembly including a knife pusher and a knife, wherein the pusher assembly and the knife pusher are advanced a first distance during a first stroke to cause a stapling of tissue and retracted a second distance greater than the first distance to engage the knife.

18. The circular stapler of claim 17, wherein the pusher assembly is configured to be advanced the second distance during a second stroke to cause a cutting of the tissue.

* * * * *